United States Patent [19]
Wettlaufer et al.

[11] Patent Number: 5,338,739
[45] Date of Patent: Aug. 16, 1994

[54] (PYRROLIDINYL)PHENYL CARBAMATES, COMPOSITIONS AND USE

[75] Inventors: David G. Wettlaufer, Phillipsburg; Peter A. Nemoto, Raritan, both of N.J.

[73] Assignee: Hoechst-Roussel Pharmaceuticals Inc., Somerville, N.J.

[21] Appl. No.: 208,554

[22] Filed: Mar. 10, 1994

[51] Int. Cl.$^5$ ............... A61K 31/40; A61K 31/535; C07D 207/12; C07D 413/06
[52] U.S. Cl. ............... 514/235.5; 514/227.8; 514/310; 514/316; 514/326; 514/343; 514/414; 514/429; 544/58.5; 544/128; 544/141; 546/147; 546/187; 546/208; 546/281; 548/465; 548/577
[58] Field of Search ............... 544/128, 141; 546/147, 546/281; 548/465, 577; 514/235.5, 310, 429

[56] References Cited

U.S. PATENT DOCUMENTS 3,149,123  9/1964  Cavalla ............... 548/577
3,646,026  2/1972  Nikles et al. ............... 548/577

OTHER PUBLICATIONS

S.-O. Thorberg, et al., Journal of Medicinal Chemistry, vol. 30, 2008–2012 (1987) entitled "Carbamate Ester Derivatives as Potential Prodrugs of the Presynaptic Dopamine Autoreceptor Agonist (−)-3-(3-Hydroxyphenyl)-N-propylpiperdine", published in the United States of America.

Primary Examiner—Robert W. Ramsuer
Attorney, Agent, or Firm—Raymond R. Wittekind

[57] ABSTRACT

Novel (pyrrolidinyl)phenyl carbamates and related compounds, intermediates and processes for the preparation thereof, and methods of relieving memory dysfunction utilizing the carbamates and related compounds, or compositions thereof are disclosed.

18 Claims, No Drawings

(PYRROLIDINYL)PHENYL CARBAMATES, COMPOSITIONS AND USE

The present invention relates to (pyrrolidinyl)phenyl carbamates and related compounds. More particularly, the present invention relates to compounds of formula 1

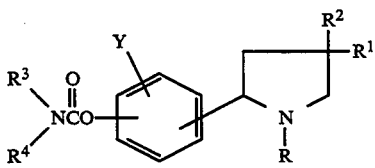

wherein:
a. R is hydrogen, loweralkyl, a group of the formula

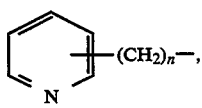

a group of the formula

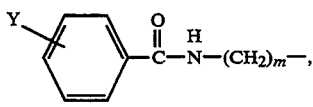

a group of the formula

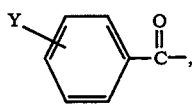

a group of the formula

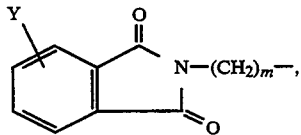

a group of the formula

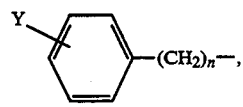

or a group of the formula

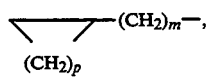

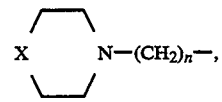

wherein X is —$CH_2$—, —O—, or —S—, Y is hydrogen, loweralkyl, loweralkoxy, hydroxy, halogen, or trifluoromethyl, and m is 1 to 5, n is 1 to 5, and p is 1,2,3,4, or 5;

b. $R^1$ and $R^2$ are independently hydrogen or loweralkyl;

c. $R^3$ and $R^4$ are independently hydrogen, loweralkyl, phenyl or phenyl substituted by one or more loweralkyl, loweralkoxy, hydroxy, halogen, or trifluoromethyl groups, or taken together with the nitrogen atom to which they are bound form a pyrrolidinyl, piperidinyl, morpholinyl, or thiomorpholinyl group, or a group of the formula

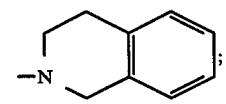

the optical isomers, or pharmaceutically acceptable salts thereof, which are useful in relieving memory dysfunction and thus are indicated in the treatment of Alzheimer's disease.

Preferred (pyrrolidinyl)phenyl carbamates and related compounds of the present invention are those wherein R is a loweralkyl, a group of the formula

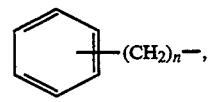

a group of the formula

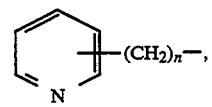

or a group of the formula

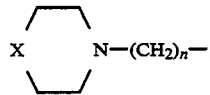

$R^3$ and $R^4$ are independently hydrogen or loweralkyl, or $R^3$ and $R^4$ taken together with the nitrogen atom to which they are bound form a group of the formula

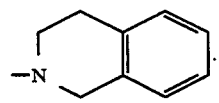

Particularly preferred are those (pyrrolidinyl)phenylcarbamates wherein X is O.

The present invention also relates to (oxopyrrolidinyl)phenyl carbamates of formula 2

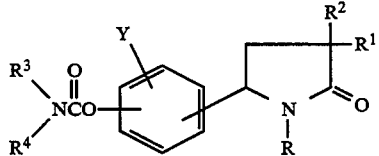

wherein:
a. R is hydrogen, loweralkyl, a group of the formula

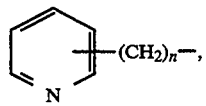

a group of the formula

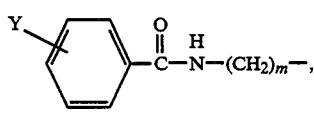

a group of the formula

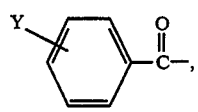

a group of the formula

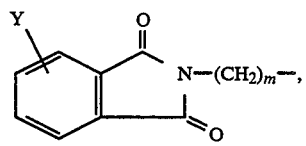

a group of the formula

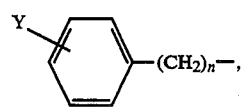

a group of the formula

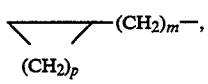

or a group of the formula

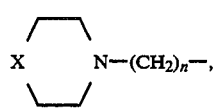

wherein X is —CH$_2$—, —O—, or —S—, Y is hydrogen, loweralkyl, loweralkoxy, hydroxy, halogen, or trifluoromethyl, and m is 1 to 5, n is 1 to 5, and p is 1,2,3,4, or 5;

b. R$^1$ and R$^2$ are independently hydrogen or loweralkyl;
c. R$^3$ and R$^4$ are independently hydrogen, loweralkyl, phenyl or phenyl substituted by one or more loweralkyl, loweralkoxy, hydroxy, halogen, or trifluoromethyl groups, or taken together with the nitrogen atom to which they are bound form a pyrrolidinyl, piperidinyl, morpholinyl, or thiomorpholinyl group, or a group of the formula

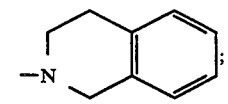

and the optical isomers, or pharmaceutically acceptable salts thereof.

The present invention also relates to (phenyl)pyrrolidines of the formula 3

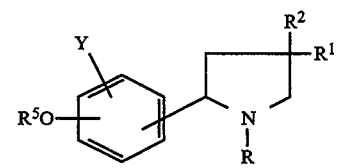

wherein:
a. R is hydrogen, loweralkyl, a group of the formula

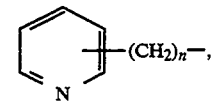

a group of the formula

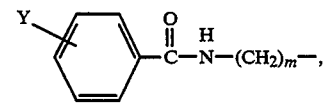

a group of the formula

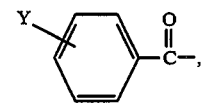

a group of the formula

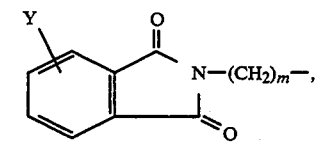

a group of the formula

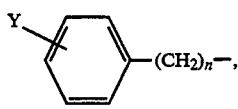

a group of the formula

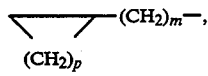

or a group of the formula

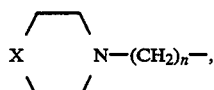

wherein X is —CH₂—, —O—, or —S—Y is hydrogen, loweralkyl, loweralkoxy, hydroxy, halogen, or trifluoromethyl, and m is 1 to 5, n is 1 to 5, and p is 1,2,3,4, or 5;

b. R¹ and R² are independently hydrogen or loweralkyl;
c. R⁵ is hydrogen or loweralkyl; the optical isomers, or pharmaceutically acceptable salts thereof, and (phenyl)pyrrolidinones of the formula 4 wherein:

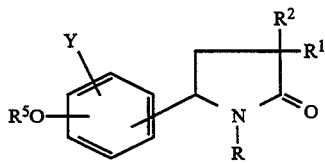

a. R is hydrogen, loweralkyl, a group of the formula

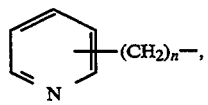

a group of the formula

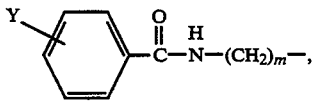

a group of the formula

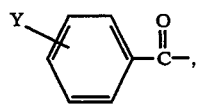

a group of the formula

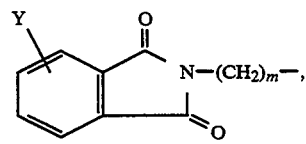

a group of the formula

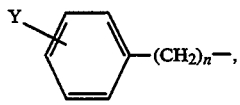

a group of the formula

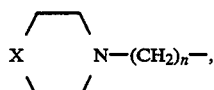

or a group of the formula

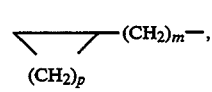

wherein X is —CH₂—, —O—, or —S—, Y is hydrogen, loweralkyl, loweralkoxy, hydroxy, halogen, or trifluoromethyl, and m is 1 or 5, n is 1 to 5, and p is 1,2,3,4, or 5;

b. R¹ and R² are independently hydrogen or loweralkyl;
c. R⁵ is hydrogen or loweralkyl; the optical isomers, or pharmaceutically acceptable salts thereof, which are useful as intermediates for the preparation of the ultimate (pyrrolidinyl)phenyl carbamates of the present invention, as well as for relieving memory dysfunction of the type associated with Alzheimer's disease.

Subgeneric thereto are compounds wherein R is a group of the formula

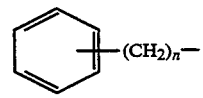

or a group of the formula

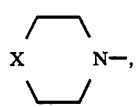

R³ and R⁴ are hydrogen or loweralkyl, or R³ and R⁴ taken together with the nitrogen atom to which they are attached form a group of the formula

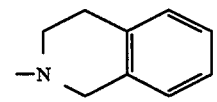

and X is O.

Subgeneric to the ultimate (pyrrolidinyl)carbamates 1 are compounds of formula

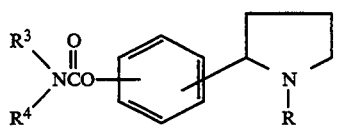

wherein:
a. R is loweralkyl, pyridinylmethyl, (4-morpholinyl)ethyl, benzoylaminoethyl, benzoyl, (1,3-dihydro-1,3-dioxo-2H-isoindolyl)ethyl, or phenylethyl; and
b. $R^3$ and $R^4$ are independently hydrogen, loweralkyl, N-morpholinylethyl, or taken together with the nitrogen atom to which they are attached form a group of the formula

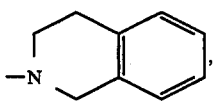

the optical isomers, or the pharmaceutically acceptable salts thereof.

As used throughout the specification and appended claims, the term "alkyl" refers to a straight or branched chain hydrocarbon radical containing no saturation and having 1 to 8 carbon atoms. Examples of alkyl groups are methyl, ethyl, 1-propyl, 2-propyl, 1-butyl, 1-hexyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The term "halogen" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel (pyrrolidinyl)phenyl carbamates are prepared by the processes delineated in Reaction Schemes A and B.

To prepare a (pyrrolidinyl)phenyl carbamate 1, a ketoacid 6 wherein $R^5$ is alkyl is esterified to a ketoester 7 wherein $R^5$ is as above and $R^6$ is alkyl which is, in turn, hydroxaminated to a oximinoester 8, reduced to an aminoester 9 and cyclized to a pyrrolidinone 10. A pyrrolidinone 10 is then converted to 1 by the pathway 10 to 11 to 12 to 13 to 1 (See Reaction Scheme A).

The esterification of 6 to 7 is perforated by successive treatment of 6 with an activator, for example, a thionyl halide 14

wherein Hal is chloro or bromo, followed by an alkanol 15

wherein $R^6$ is as defined above at about ambient temperature. The esterification may also be performed by any one of the numerous methods known in the art.

The hydroxamination of 7 to 8 is accomplished by contacting a ketoester 7 with hydroxylamine as a hydrohalide 16

wherein Hal is as above in the presence of an acid acceptor such as, for example, pyridine or a methylpyridine (picoline, lutidine, or s-collidine) at a temperature within the range of about ambient to about 150° C. Elevated temperatures, steam bath temperatures, are preferred.

The reduction of 8 to 9 is effected by means of hydrogen in the presence of a hydrogenation catalyst in a suitable solvent. Among hydrogenation catalysts, there may be mentioned platinum, palladium, rhodium, and ruthenium, free or supported on carbon, barium carbonate, and the like. Among suitable solvents, there may be mentioned alkanols, for example, methanol, ethanol, 1-, or 2-propanol, and the like. A catalyst-solvent system consisting of palladium-on-carbon is preferred. The reduction (hydrogenation) pressure and temperature are not narrowly critical. The reduction proceeds readily at a pressure of 50 pounds per square inch and at a temperature of about 50° C.

The cyclization of 9 to 10 is achieved by heating an aminoester 9 in an inert solvent at the reflux temperature of the medium. Suitable inert solvents are benzene, toluene, xylene, and the like. Toluene is preferred.

A (pyrrolidinyl)phenyl carbamate 1 is elaborated by reducing a pyrrolidinone 10 wherein $R^5$ is alkyl to a pyrrolidine 11, acylating 11 to an N-acylpyrrolidine 12 and, in turn, cleaving 12 to a phenol 13, and carbamylating 13 to an ultimate phenyl carbamate 1.

The reduction of a pyrrolidinone 10 to a pyrrolidine 11 is effected by an alkali metal aluminum hydride, for example, lithium, sodium, or potassium aluminumhydride in an ethereal solvent, for example, tetrahydrofuran, ether and the like, at the reflux temperature of the reduction medium.

The subsequent alkylation of a pyrrolidine 11 to an N-alkylpyrrolidine 12, cleavage of an alkoxyphenol 12 to a phenol 13, and carbamylation of 13 to an ultimate carbamate 1 is effected by the processes hereinafterdescribed for the conversion of 17 to 18 to 2.

To prepare a pyrrolidinone carbamate 2, a pyrrolidinone 10 is alkylated to an N-alkylpyrrolidinone 17, cleaved to a phenol 18 and carbarmylated to a carbamoylbenzene 2. (See Reaction Scheme B). The alkylation is effected by forming a salt of a pyrrolidinone 17 with a alkali metal hydride (e.g., lithium, potassium, or sodium hydride) in a dipolar aprotic solvent (e.g., dimethylacetamide, dimethylformamide, hexamethylphosphoramide, or dimethylsulfoxide) at about ambient temperature and treating the salt with a halide 19, RHal 19 wherein Hal is as above, optimally in the presence of an alkylation promoter (e.g., an alkali metal halide such as sodium or potassium bromide or iodide), preferably at an elevated temperature consistent with the solvent of the alkylation medium. A reaction temperature of about 110° C. is preferred when dimethylformamide is used as the solvent. Potassium iodide is the preferred alkylation promoter.

The cleavage of 17 is performed in a hydrohalic acid such as hydriodic acid or hydrobromic acid, hydrobromic acid being preferred, at an elevated temperature of about 80° C. to 120° C., a cleavage temperature of about 100° C. being preferred.

The carbamylation of 18 to 2 is carried out by treating a phenol 18 with an isocyanate 20

$R^2N=C=O$ 20 wherein $R^2$ is as hereinbefore defined in an ethereal solvent in the presence of an alkali metal bicarbonate or carbonate at about ambient temperature. Included among ethereal solvents are 1,2-dimethoxyethane, 2-methoxyethyl ether, tetrahydrofuran, dioxane, and the like. Tetrahydrofuran is the preferred solvent. Included among alkali metal bicarbonates and carbonate are lithium, sodium, and potassium bicarbonates and carbonates. Potassium carbonate is preferred.

The carbamylation of 18 to 2 is also effected by treatment of a phenol 18 with a 1,1'-carbonyldiimidazole followed by an amine 21

$R^3R^4NH$ 21 where $R^3$ and $R^4$ are as hereinbeforedefined in an ethereal solvent selected from the group mentioned above, tetrahydrofuran being preferred, at about ambient temperature.

The (pyrrolidinyl)phenyl carbamates and related compounds of the present invention are useful as agents for the relief of memory dysfunction, particularly dysfunctions associated with decreased cholinergic activity such as those found in Alzheimer's disease. Relief of memory dysfunction activity is demonstrated in the in vitro inhibition of acetylcholinesterase assay, an assay for the determination of the ability of a drug to inhibit the inactivation of acetylcholine, a neurotransmitter implicated in the etiology of memory dysfunction and Alzheimer's dementia. In this assay, a modification of a test described by G. L. Ellman, et al., Biochemical Pharmacology, 7, 88 (1961), the following reagents are prepared and employed:

1. 0.05M Phosphate Buffer (pH 7.2)

A solution of monobasic sodium phosphate monohydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate in Buffer

The 0.05M Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic acid in Buffer

The 0.05M Phosphate Buffer (pH 7.2) was added to 5,5-dithiobisnitrobenzoic acid to a total volume of 100 ml, i.e., a quantity sufficient (gs) to 100 ml.

4. Stock Solution of Drug

A 2 millimolar stock solution of the test drug is prepared in a quantity sufficient of either acetic acid or dimethyl sulfoxide to volume with 5,5-Dithiobisnitrobenzene Acid in Buffer. Stock Solution of Drug is serially diluted (1:10) so that the final cuvette concentration is $10^{-4}$ molar.

Male Wistar rates are decapitated, brains rapidly removed, corpora striata dissected free, weighed and homogenized in 19 volumes (approximately 7 mg protein/ml) of 0.05M phosphate Buffer (pH 7.2) using a Potter-Elvehjem homogenizer. A 25 $\mu$l aliquot of this suspension is added to 1 ml of the vehicle or various concentrations of the test drug and preincubated for 10 minutes at 37° C. Enzyme activity is measured with a Beckman DU-50 spectrophotometer with the following software and instrument settings:

1. Kinetics Soft-Pac TM Module #598273;
2. Program #6 Kindata;
3. Source—Vis;
4. Wavelength—412 nm;
5. Sipper—none;
6. Cuvettes—2 ml cuvettes using auto 6-sampler;
7. Blank—1 for each substrate concentration;
8. Interval time—15 seconds (15 or 30 seconds for kinetics);
9. Total time—5 minutes (5 or 10 minutes for kinetics);
10. Plot—yes;
11. Span—autoscale;
12. Slope—increasing;
13. Results—yes (gives slope); and
14. Factor—1.

Reagents are added to the blank and sample cuvettes as follows:

| 1. | Blank: | 0.8 ml 5,5-Dithiobisnitrobenzoic Acid |
| | | 0.8 ml Substrate in Buffer |
| 2. | Control: | 0.8 ml 5,5-Dithiobisnitrobenzoic Acid/Enzyme |
| | | 0.8 ml Substrate in Buffer |
| 3. | Drug: | 0.8 ml 5,5-Dithiobisnitrobenzoic Acid/Drug/Enzyme |
| | | 0.8 ml Substrate in Buffer |

Blank values are determined for each run to control for non-enzymatic hydrolysis of substrate and these values are automatically subtracted by the Kindata program available on kinetics soft-pac module. This program also calculates the rate of absorbance change for each cuvette.

For IC$_{50}$ Determinations

Substrate concentration is 10 millimolar diluted 1:2 in assay yielding final concentration of 5 millimolar. 5,5-Dithiobisnitrobenzoic acid concentration is 0.5 millimolar yielding 0.25 millimolar final concentration.

$$\% \text{ Inhibition} = \frac{\text{Slope Control} - \text{Slope drug}}{\text{Slope Control}} \times 100$$

IC$_{50}$ values are calculated from log-probit analysis

TABLE I

| Compound | Inhibition of Acetylcholinesterase Activity IC$_{50}$($\mu$M) |
| --- | --- |
| 3-[1-(4-Pyridinylmethyl)-2-pyrrolidinyl] phenyl methylcarbamate | 0.0244 |
| 3-{1-[2-(4-Morpholinyl)ethyl]-5-oxo-2-pyrrolidinyl}phenyl methylcarbamate | 18.74 |
| 3-[1-((4-Pyridinyl)methyl)-5-oxo-2-pyrrolidinyl]phenyl methylcarbamate | 1.442 |
| 3-{1-[(4-Pyridinyl)methyl]2-pyrrolidinyl} pehnyl 3,4-dihydro-2(1H)-isoquinoline carbamate | 0.5685 |
| 3-{1-[2-(4-morpholinyl)ethyl]-2-pyrrolidinyl} phenyl methylcarbamate | 0.5287 |
| physostigmine (standard) | 0.13 |

Relief of memory dysfunction activity is also determined in the ex vivo inhibition acetylcholinesterase assay, an assay also for the determination of the ability of a drug to inhibit the inactivation of acetylcholine. In this assay a modification of a test also described by G. L. Ellman, et al, Biochemical Pharmacology, 7, 88 (1961), the following reagents are prepared and employed:

A dose-response for cholinesterase inhibition is determined. A dose which give a reasonable effect (>50% inhibition if possible) is chosen to do the time-course experiment. The effects on brain acetylcholinesterase activity are examined in striatal tissue or forebrain, using 5 mM acetylthiocholine as a substrate.

1. 0.05M Phosphate Buffer (pH 7.2)

A solution of monobasic sodium phosphate monohydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate in Buffer

The 0.05M Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic acid in Buffer

The 0.05M Phosphate Buffer (pH 7.2) was added to 5,5-dithiobisnitrobenzoic acid to a total volume of 100 ml, i.e., a quantity sufficient (gs) to 100ml.

Groups of four male Wistar rats are given vehicle or the test drug orally. For the initial dose-response study, the rats are given varying doses of test drug and sacrificed at 1 hour after dosing. The animals are observed and the occurrence of cholinergic signs is noted (piloerection, tremors, convulsions, salivation, diarrhea and chromodacryorrhea). For the time-course study, a dose of the test drug is given which gave significant inhibition of cholinesterase activity.

The rats are decapitated, brains rapidly removed, corpora striata or forebrain dissected free, weighed and homogenized in 4 volumes of 0.05M phosphate buffer, pH 7.2 using a Potter-Elvehjem homogenizer (Kontes, Vineland, N.J.). A 12.5 $\mu$l aliquot of the homogenate is added to 1 ml 5,5-dithiobisnitrobenzoic acid in buffer. Enzyme activity is measured with the Beckman DU-50 spectrophotometer.

Instrument Settings
Kinetics Soft-Pac Module #598273 (10)
Program #6 Kindata
Source—Vis
Wavelength—412 nm
Sipper—none
Cuvettes—2 ml cuvettes using auto 6-sampler
Blank—1 for each substrate concentration
Interval time—15 seconds
Total time—3 minutes
Plot—no
Span—autoscale
Slope—increasing
Results—yes (gives slope)
Factor—1

Reagents are added to the blank and sample cuvettes as follows;

| | |
| --- | --- |
| Blank: | 0.8 ml 5,5-dithiobisnitrobenzoic acid in buffer |
| | 0.8 ml substrate in buffer |
| Control: | 0.8 ml 5,5-dithiobisnitrobenzoic acid in buffer |
| | 0.8 ml substrate in buffer |
| Drug: | 0.8 ml 5,5-dithiobisnitrobenzoic acid in buffer |
| | 0.8 ml substrate in buffer. |

Blank values are determined for each run to control for non enzymatic hydrolysis of substrate and these values are automatically subtracted by the kindata program available on kinetics soft-pac module. This program also calculates the rate of absorbance change for each cuvette.

Substrate concentration is 10 mM diluted 1:2 in assay yielding final concentration of 5 mM. 5,5-dithiobisnitrobenzoic acid concentration is 0.5 mM yielding 0.25 mM final concentration. The percent inhibition at each dose or time is calculated by comparison with the enzyme activity of the vehicle control group.

$$\% \text{ Inhibition} = \frac{\text{Slope Control} - \text{Slope drug}}{\text{Slope Control}} \times 100$$

TABLE II

| Compound | Dose mg/kg per os | Inhibition of Acetylcholinesterase Activity Percent Inhibition @ 1 hr |
| --- | --- | --- |
| 3-[1-(4-pyridinylmethyl)-2-pyrrolidinyl] phenyl methylcarbamate | 10 | 80%[a] |
| 3-[1-ethyl-2-pyrrolidinyl]phenyl methylcarbamate | 1 | 73%[b] |
| 3-[1-(3-pyridinylmethyl)-2-pyrrolidinyl]phenyl methylcarbamate | 10 | 51%[b] |
| 3-[1-(2-phenylethyl)-2-pyrrolidinyl]phenyl methylcarbamate | 10 | 25%[b] |
| physostigmine (standard) | 0.3[c] | 27%[b] |

[a]striatum
[b]forebrain
[c]intraperitoneal

Relief of memory dysfunction is achieved when the present (pyrrolidinyl)phenyl carbamates and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention. Compounds of the invention include;

a. 2-methyl-3-[1-(4-pyridinylmethyl)-2-pyrrolidinyl]-phenyl methylcarbamate;
b. 4-methoxy-3-[1-(4-pyridinylmethyl)-2-pyrrolidinyl]-phenyl methylcarbamate;
c. 6-hydroxy-3-[1-(4-pyridinylmethyl)-2-pyrrolidinyl]-phenyl methylcarbamate;
d. 6-chloro-3-[1-(4-pyridinylmethyl)-2-pyrrolidinyl]-phenyl methylcarbamate;
e. 3-[1-(4-pyridinylmethyl)-2-pyrrolidinyl]-5-trifluoromethylphenyl methylcarbamate;
f. 3-(2-pyrrolidinyl)phenyl methylcarbamate;
g. 3-(1-methyl-2-pyrrolidinyl)phenyl methylcarbamate;
h. 3-[(1-cyclopropylmethyl)-2-pyrrolidinyl]phenyl methylcarbamate;
i. 4-{1-[2-(N-thiomorpholinyl)ethyl]-2-pyrrolidinyl}phenyl methylcarbamate;
j. 4-{1-[2-(1-piperidinyl)ethyl]-2-pyrrolidinyl}phenyl methylcarbamate;
k. 3-[1-(4-pyridinylmethyl)-4-methyl-2-pyrrolidinyl]-phenyl methylcarbamate;
l. 3-[1-(4-pyridinylmethyl)-4,4-dimethyl-2-pyrrolidinyl]phenyl methylcarbamate;
m. 4-{1-[2-(1-methyl-4-piperidinyl)ethyl]-2-pyrrolidinyl}phenyl phenylcarbamate;
n. 4-{1-[2-(1-piperidinyl)ethyl]-2-pyrrolidinyl}phenyl 4-methylphenylcarbamate;
o. 3-{1-[2-(1-piperidinyl)ethyl]-2-pyrrolidinyl}phenyl phenylcarbamate;
p. 4-{1-[2-(1-piperidinyl)ethyl]-2-pyrrolidinyl}phenyl 3-chlorophenylcarbamate;
q. 4-{1-[2-(1-piperidinyl)ethyl]-2-pyrrolidinyl}phenyl 4-trifluoromethylcarbamate;
r. 4-{1-[2-(1-piperidinyl)ethyl]-2-pyrrolidinyl}phenyl 3,4-dichlorophenylcarbamate;
s. 4-{1-[2-(1-piperidinyl)ethyl]-2-pyrrolidinyl}phenyl pyrrolidinylcarbamate;
t. 4-{1-[2-(1-piperidinyl)ethyl]-2-pyrrolidinyl}phenyl 1-piperidinylcarbamate;
u. 4-}1-[2-(1-piperidinyl)ethyl]-2-pyrrolidinyl}phenyl 4-morpholinylcarbamate;
v. 3-{1-[3-(4-morpholinyl)propyl]-2-pyrrolidinyl}phenyl methylcarbamate;
w. 3-{1-[4-(4-morpholinyl)butyl]2-pyrrolidinyl}phenyl methylcarbamate;
x. 3-{1-[5-(4-morpholinyl)pentyl]-2-pyrrolidinyl}phenyl methylcarbamate;
y. 4-{1-[3-(4-morpholinyl)propyl]-5-oxo-2-pyrrolidinyl}phenyl methylcarbamate;
z. 4-{1-[4-(4-morpholinyl)butyl]-5-oxo-2-pyrrolidinyl}phenyl methylcarbamate;
a'. 4-{1-[5-(4-morpholinyl)pentyl]-5-oxo-2-pyrrolidinyl}phenyl methylcarbamate.

Also included are all precursors of the compounds of the invention.

Effective mounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl, salicylate, or orange flavoring may be added. When the dosage unit is a capsule, it may contain, in addition to materials of the above type, a liquid carder such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

5-(3-Methoxyphenyl)-2-pyrrolidinone

To a stirred solution of 4-(3-methoxyphenyl)-4-oxobutanoic acid (26.5 g), prepared by the method described by R. M. Schlisa and W. C. Hammas in the Journal of Organic Chemistry, 38, 3224 (1973), in absolute ethanol (425 ml) was added thionyl chloride (18.6 ml) at ambient temperature, under nitrogen. The reaction mixture was stirred for 24 hrs, concentrated, and the mixture was diluted with pyridine (85 ml). Hydroxylamine hydrochloride (13.3 g) was added, and the mixture was heated on a steam bath for 0.5 hr to 1.5 hrs. The reaction mixture was cooled to ambient temperature and diluted with 5% hydrochloric acid and ether. The layers were separated, and the aqueous phase was extracted with ether (2 times). The combined organic extracts were washed with 5% hydrochloric acid (4 times), washed with brine, dried over anhydrous magnesium sulfate, filtered, and the filtrate was concentrated. The residue was purified by flash column chromatography (silica gel, 15% ethyl acetate/hexane). The appropriate fractions were collected and evaporated to afford 27.4 g (86%) of 4-(3-methoxyphenyl)-4-oxobutanoic acid oxime.

4-(3-Methoxyphenyl)-4-oxobutanoic acid oxime in ether was passed through a column of activated carbon and a 11.0 g portion was dissolved in absolute ethanol ( 190 ml) and reduced by hydrogen in the presence of 10% palladium-on-carbon (1.10 g) at 50 psig and 50° C. over 6.5 hrs. The mixture was filtered through a pad of celite, and the filter cake was washed with methanol. Concentration of the filtrate afforded 9.39 g (90%) of ethyl 4-amino-4-(3-methoxyphenyl)butanoate.

Ethyl 4-amino-4-(3-methoxyphenyl)butanoate (9.39 g) was dissolved in toluene (50 ml) and the solution heated under reflux for 0.5 hr to 1.0 hr. The mixture was cooled to ambient temperature, the precipitate was collected, and the filtrate was concentrated. The residue was recrystallized from ether to give 6.80 g (90%) of product, mp 84°-85° C.

Analysis: Calculated for $C_{11}H_{13}NO_2$: 69.09%C 6.85%H 7.32%N Found: 69.04%C 7.08%H 7.34%N

EXAMPLE 2

1-Cyclopropylmethyl-2-(3-methoxyphenyl)pyrrolidine salicylate

To a stirred solution of 5-(3-methoxyphenyl)-2-pyrrolidinone (5.00 g) and tetrahydrofuran (260 ml), at ambient temperature, under nitrogen, was added lithium aluminum hydride (39.3 ml, 1M in tetrahydrofuran). The mixture was heated under reflux for 6 hrs, cooled to ambient temperature, and aqueous tetrahydrofuran was added slowly. The suspension was concentrated, and the residue was dissolved in dilute aqueous sulfuric acid. The solution was made basic (pH 12) by the slow addition of aqueous sodium hydroxide solution. The mixture was extracted with dichloromethane (3 times) and ether (1 time). The combined organic extracts were washed with brine, dried over anhydrous potassium carbonate, filtered, and the filtrate was concentrated to give 2-(3-methoxyphenyl)pyrrolidine.

2-(3-Methoxyphenyl)pyrrolidine (4.40 g) was dissolved in acetonitrile (50–60 ml), and the solution was treated with milled potassium carbonate (5.15 g) and cyclopropylmethyl bromide (2.20 ml). The suspension was heated under reflux, under nitrogen, for 5 hrs, cooled to ambient temperature, and dichloromethane and water were added. The layers were separated, and the organic layer was washed with brine, dried over anhydrous potassium carbonate and filtered. The filtrate was concentrated, and the residue was purified by flash column chromatography (silica gel, 30% ether/hexane). The appropriate fractions were collected and concentrated to afford 1.86 g (35.5%) of product free base. The salicylate, prepared with salicylic acid (1.05 eq) in ether followed by absolute ethanol, had mp 105°–107° C.

Analysis: Calculated for $C_{22}H_{27}NO_4$: 71.52%C 7.37%H 3.79%N Found: 71.39%C 7.38%H 3.78%N

EXAMPLE 3

3-[1-(4-Pyridinylmethyl)-2-pyrrolidinyl]phenol

To a stirred solution of 2-(3-methoxyphenyl)pyrrolidine (5.42 g) in dry dichloromethane (153 ml) was added sodium hydride (97%, 1.69 g) followed by 4-picolyl chloride hydrochloride (5.26 g), under nitrogen, at 0° C. The reaction mixture was stirred for 15 hrs at ambient temperature and diluted with water and ethyl acetate. The layers were separated, and the aqueous phase was extracted with ethyl acetate (4 times). The combined organic extracts were washed with brine, dried over anhydrous magnesium sulfate, filtered, and the filtrate was concentrated. The residue was purified by flash column chromatography (silica gel, 2% triethylamine/ether). The appropriate fractions were collected and evaporated to afford 5.70 g (70%) of 2-(3-methoxyphenyl)-1-(4-pyridinylmethyl)pyrrolidine.

2-(3-Methoxyphenyl)-1-(4-pyridinylmethyl)pyrrolidine (5.70 g) was dissolved in dry dichloromethane (66 ml) and cooled to −78° C., under nitrogen. Boron tribromide in dichloromethane (1.0M solution, 66.0 ml) was added dropwise, and the reaction mixture was allowed to warm to ambient temperature overnight. The mixture was acidified with 5% hydrochloric acid to pH of 2 and then basified with saturated sodium bicarbonate solution to pH of 8. The layers were separated, and the aqueous phase was extracted with dichloromethane (3 times) and ether (1 time). The organic extracts were washed with brine, dried over anhydrous potassium carbonate, filtered, and the filtrate was concentrated. The residue was purified by flash column chromatography (silica gel, 2% triethylamine/ether). The appropriate fractions were collected and concentrated to afford 1.60 g (30%) of product. Recrystallization from ether gave the analytical sample, mp 138° C.

Analysis: Calculated for $C_{16}H_{18}N_2O$: 75.56%C 7.13%H 11.01%N Found: 75.28%C 7.19%H 10.90%N

EXAMPLE 4

3-[1-(4-Pyridinylmethyl)-2-pyrrolidinyl]phenyl methylcarbamate

To a stirred solution of 3-[1-(4-pyridinylmethyl)-2-pyrrolidinyl]phenol (0.60 g) in dry tetrahydrofuran (16 ml) was added milled potassium carbonate (0.36 g), followed by methyl isocyanate (0.15 ml), dropwise, at ambient temperature, under nitrogen, with stirring. The mixture was stirred for 17 hrs and filtered through a pad of celite. The filter cake was washed with ethyl acetate, and the filtrate was concentrated. The residue was purified by flash column chromatography (silica gel, ether). The appropriate fractions were collected and concentrated to afford 0.63 g (86%) of product. Trituration of the residue with petroleum ether gave the analytical sample, mp 92°–105° C.

Analysis: Calculated for $C_{18}H_{21}N_3O_2$: 69.43%C 6.80%H 13.49%N Found: 69.26%C 6.78%H 13.38%N

EXAMPLE 5

3-{1-[2-(4-Morpholinyl)ethyl]-5-oxo-2-pyrrolidinyl}phenyl methylcarbamate

To a suspension of pentane washed sodium hydride (80% oil dispersion, 4.2 g) in dry dimethylformamide (280 ml) was added 5-(3-methoxyphenyl)-2-pyrrolidinone (16.0 g) followed by N-(2-chloroethyl)morpholine hydrochloride (16.4 g) and potassium iodide (0.15 g) at ambient temperature. The solution was heated at 110° C. for 1.5 hrs and then cooled to ambient temperature. The reaction mixture was quenched with saturated aqueous ammonium chloride solution (30 ml), and the dimethylformamide was removed by Kugelrohr distillation. The residue was diluted with water and ethyl acetate. The layers were separated and the aqueous phase was extracted with ethyl acetate (4 times). The combined organic extracts were washed with brine, dried over anhydrous sodium sulfate, filtered, and the filtrate was concentrated. The residue was flushed through a column of silica gel (ether/0–10% methanol). The appropriate fractions were collected and evaporated to give 12.8 g (50%) of 5-(3-methoxyphenyl)-1-[2-(4-morpholinyl)ethyl]-2-pyrrolidinone.

5-(3-Methoxyphenyl)-1-[2-(4-morpholinyl)ethyl]-2pyrrolidinone (12.8 g) was dissolved in 48% hydrobromic acid (100 ml) and warmed at 100° C. for 4.5 hrs. The reaction mixture was cooled to ambient temperature, neutralized with saturated sodium bicarbonate solution, and the mixture was extracted with dichloromethane (6 times). The combined organic extracts were washed with brine, dried over anhydrous sodium sulfate, filtered, and the filtrate was concentrated. The residue was purified by flash column chromatography (silica gel, ether). The appropriate fractions were collected and concentrated to give 3.3 g (55%) of 5-(3-hydroxyphenyl)-1-[2-(4-morpholinyl)ethyl]-2-pyrrolidinone.

To a solution of 5-(3-hydroxyphenyl)-1-[2-(4-morpholinyl)ethyl]-2-pyrrolidinone (1.1 g) in dry tetrahydrofuran (50 ml) was added methyl isocyanate (0.26 ml) at ambient temperature, with stirring, over ten mins. Milled potassium carbonate was added, and the reaction mixture was stirred for 17 hrs. The mixture was filtered through a pad of celite. The filter cake was washed with ethyl acetate and the combined filtrates were concentrated. The residue was purified by flash column chromatography (silica gel, ether/0–50% methanol). The appropriate fractions were collected and concentrated to give 1.2 g (89%) of product. Crystallization of the residue from ether gave the analytical sample, mp 100°–102° C.

Analysis: Calculated for $C_{18}H_{25}N_3O_4$: 62.23%C 7.25%H 12.09%N Found: 62.16%C 7.18%H 12.09%N

EXAMPLE 6

3-[1-(4-Pyridinylmethyl)-2-pyrrolidinyl]phenyl 3,4-dihydro-2(1H)-isoquinoline carbamate hemifumarate To a stirred solution of 3-[1-(4-pyridinylmethyl)-2-pyrrolidinyl]phenol (1.1 g) in dry tetrahydrofuran (30 ml) was added 1,1'-carbonyldiimidazole (1.4 g) at ambient temperature, under nitrogen. After 24 hrs, additional 1,1'-carbonyldiimidazole (200 mg) was added. The reaction mixture was stirred for 5 hrs, acetic acid (1.2 ml) followed by 1,2,3,4-tetrahydroisoquinoline (1.2 ml) was added. The solution was stirred for 41.5 hrs and diluted with saturated sodium bicarbonate solution and ether. The layers were separated, and the aqueous phase was extracted with ether (2 times). The combined organic extracts were washed with brine, dried over anhydrous sodium sulfate, filtered, and the filtrate was concentrated. The residue was purified by flash column chromatography (silica gel, 1:1 ethyl acetate/dichloromethane) and (silica gel, ether). The appropriate fractions were collected and concentrated to give 0.70 g (39%) of product. The hemifumarate salt was prepared in ethanol with fumaric acid (2.1 equivalents) and had mp 147°–150° C.

Analysis: Calculated for $C_{28}H_{29}N_3O_4$: 71.31%C 6.20%H 8.91%N Found: 71.13%C 6.06%H 8.81%N

EXAMPLE 7

3-{1-[2-(4-Morpholinyl)ethyl]-2-pyrrolidinyl}phenyl methylcarbamate bis-fumarate To a suspension of petroleum ether washed sodium hydride (80% oil dispersion, 2.5 g) in dry dimethylformamide (150 ml) was added 2-(3-methoxyphenyl)pyrrolidine (7.8 g) followed by N-(2-chloroethyl)morpholine hydrochloride (8.6 g) and potassium iodide at ambient temperature, under nitrogen. The reaction mixture was heated at 110° C. for 4 hrs, allowed to cool to ambient temperature, quenched with saturated aqueous ammonium chloride solution (10 ml), and distilled in a Kugelrohr apparatus. The residue was dissolved in water and ethyl acetate. The layers were separated, and the aqueous phase was extracted with ethyl acetate (4 times). The combined organic extracts were dried over anhydrous sodium sulfate, filtered, and the filtrate was concentrated. The residue was purified by flash column chromatography (silica gel, ethyl acetate). The appropriate fractions were collected and concentrated to afford 3.6 g (28%) of 1-[2-(4-morpholinyl)ethyl]-2-(3-methoxyphenyl)pyrrolidine.

1-[2-(4-Morpholinyl)ethyl]-2-(3-methoxyphenyl) pyrrolidine (3.6 g) in 48% hydrobromic acid (50 ml) was heated at 100° C. for 8.5 hrs. The reaction mixture was cooled to ambient temperature, neutralized with saturated sodium bicarbonate solution and diluted with dichloromethane. The layers were separated and the aqueous phase was extracted with dichloromethane (3 times). The combined organic extracts were washed with brine, dried over anhydrous sodium sulfate, filtered, and the filtrate was concentrated. The residue was purified by flash column chromatography (silica gel, ether). The appropriate fractions were collected and concentrated to give 2.0 g (59%) of 3-{1-[2-(4-morpholinyl)ethyl]-2-pyrrolidinyl}phenol.

To a solution of 3-{1-[2-(4-morpholinyl)ethyl]-2-pyrrolidinyl}phenol (1.3 g) in dry tetrahydrofuran (50 ml) was added methyl isocyanate (0.29 ml) at ambient temperature, under nitrogen, with stirring for ten mins. Milled potassium carbonate (0.7 g) was added. The reaction mixture was stirred for 18.5 hrs, filtered through a pad of celite, and the filter cake was washed with ethyl acetate. The combined filtrates were concentrated. The residue was purified by flash column chromatography (silica gel, ether/0–25% methanol). The appropriate fractions were collected and concentrated to yield 1.2 g (80%) of product. The bis-fumarate salt was prepared in ethanol with fumaric acid (2.1 equivalents) and had mp 162°–164° C.

Analysis: Calculated for $C_{26}H_{35}N_3O_{11}$: 55.22%C 6.24%H 7.43%N Found: 55.12%C 6.19%H 7.18%N

EXAMPLE 8

5-(4-Methoxyphenyl)-2-pyrrolidinone

To a stirred solution of 4-(4-methoxyphenyl)-4-oxobutanoic acid (100 g) in absolute ethanol (960 ml) was added thionyl chloride (70.0 ml) at ambient temperature, under a nitrogen flush, with stirring, for 18 hrs. The reaction mixture was concentrated, the residue was dissolved in pyridine (310 ml), and hydroxylamine hydrochloride (50.0 g) was added. The reaction mixture was heated over steam (1.5 hrs), cooled to ambient temperature, diluted with water (6 L) and extracted with ether (3 times). The combined ether extracts were back-washed with 5% aqueous hydrochloric acid until the washings were acidic. The layer was washed with brine, dried over anhydrous magnesium sulfate, decolorized with activated charcoal, filtered, and the filtrate was concentrated to give ethyl 4-(4-methoxyphenyl)-4-oxobutanoate oxime.

Ethyl 4-(4-methoxyphenyl)-4-oxobutanoate oxime (15.0 g) was hydrogenated in absolute ethanol (220 ml) and methanolic hydrochloric acid (15 ml) with 10% palladium-on-carbon (1.5 g) at 55 psig and 60° C. for 3 hrs. The catalyst was filtered through a pad of celite and the filtrate was recharged with catalyst and hydrogenated (as above) for 5 hrs. The catalyst was removed by filtration through a pad of celite and washed with methanol. Concentration of the filtrate afforded ethyl 4-amino-4-(4-methoxy)phenyl butanoate hydrochloride.

Ethyl 4-amino-4-(4-methoxy)phenyl butanoate hydrochloride was slurried in toluene (150 ml) and triethyl amine (12.5 ml). The mixture was heated under reflux 2 hrs, cooled to ambient temperature, filtered through a pad of celite, and the filter cake was washed with toluene. The filtrate was concentrated, and the precipitate was collected. The filter cake was dissolved in dichloromethane and aqueous sodium bicarbonate solution, and the layers were separated. The organic layer was washed with aqueous sodium bicarbonate solution, and the combined aqueous layers back-extracted with dichloromethane. The combined organic layers were washed with brine, dried over anhydrous potassium carbonate and filtered, and partially concentrated to give 1.48 g of product, mp 133.5°–135° C. The mother liquid was concentrated to afford an additional 4.48 g of product (total yield 5.97 g (51.9%).

Analysis: Calculated for $C_{11}H_{13}NO_2$: 69.09%C 6.85%H 7.32%N Found: 69.02%C 6.88%H 7.34%N

EXAMPLE 9

5-(4-Hydroxyphenyl)-1-[2-(4-morpholinyl)ethyl]-2-pyrrolidinone

To a suspension of pentane washed sodium hydride (80% oil dispersion, 5.18 g) in dry dimethylformamide (275 ml) was added 5-(4-methoxyphenyl)pyrrolidin-2-one (16.0 g) followed by N-(2-chloroethyl)morpholine hydrochloride (15.5 g) and potassium iodide (0.05 g) at ambient temperature. The solution was heated at 110° C. for 1.5 hrs, cooled to ambient temperature, and quenched with saturated aqueous ammonium chloride solution. The mixture was concentrated in a Kugelrohr apparatus. The residue was diluted with water and ethyl acetate, the layers were separated, and the aqueous phase was extracted with ethyl acetate (4 times). The combined organic extracts were washed with brine, dried over anhydrous potassium carbonate, filtered, and the filtrate was concentrated. The residue was purified by preparative high performance liquid chromatography (silica gel, 1% triethylamine/1% methanol/ethyl acetate). The appropriate fractions were collected and concentrated to afford 18.2 g (72.8%) of 5-(4-methoxyphenyl)-1-[2-(4-morpholinyl)ethyl]-2-pyrrolidinone. 5-(4-Methoxyphenyl)-1-[2-(4-morpholinyl)ethyl]-2-pyrrolidinone (8.82 g) was dissolved in 48% hydrobromic acid (50 ml) and warmed at 100° C. for 5 hrs. The reaction mixture was cooled to ambient temperature, neutralized with saturated sodium bicarbonate solution and extracted with dichloromethane (6 times). The combined organic extracts were washed with brine, dried over anhydrous sodium sulfate, filtered, and the filtrate was concentrated. Dilution of the residue with dichloromethane and ether gave the analytical sample (1.99 g), mp 143°–144° C. The mother liquor was concentrated to give a total of 6.20 g (74.0%) of product.

Analysis: Calculated for $C_{16}H_{22}N_2O_3$: 66.19%C 7.64%H 9.65%N Found: 66.27%C 7.66%H 9.57%N

EXAMPLE 10

4-{1-[2-(4-Morpholinyl)ethyl]-5-oxo-2-pyrrolidinyl} phenyl methylcarbamate

To a solution of 5-(4-hydroxyphenyl)-1-[2-(4-morpholinyl)ethyl]pyrrolidin-2-one (0.99 g) in dry tetrahydrofuran (50 ml) was added methyl isocyanate (0.22 ml) at ambient temperature, with stirring, over ten mins. Milled potassium carbonate (0.565 g) was added, the reaction mixture was stirred for 2 days and filtered through a pad of celite. The filter cake was washed with ethyl acetate, and the combined filtrates were concentrated. The residue was purified by flash column chromatography (silica gel, 1% triethylamine/1–10% methanol/ether) and (silica gel, 5% methanol/ether). The appropriate fractions were collected and concentrated to afford 0.62 g (52.3%) of product. Recrystallization from absolute ethanol/ether gave the analytical sample, mp 119°–120° C.

Analysis: Calculated for $C_{18}H_{25}N_3O_4$: 62.23%C 7.25%H 12.09%N Found: 61.86%C 7.18%H 11.88%N

EXAMPLE 11

4-{1-[2-(4-Morpholinyl)ethyl]-2-pyrrolidinyl}phenol

To a stirred solution of lithium aluminum hydride (2.26 g) and tetrahydrofuran (185 ml) was added 5-(4-methoxyphenyl)pyrrolidin-2-one in tetrahydrofuran (250 ml). The mixture was heated under reflux for 6 hrs, cooled to ambient temperature, and water (2.5 ml) in tetrahydrofuran and 15% aqueous sodium hydroxide solution (2.5 ml) were added slowly. Additional water (8.5 ml) was added. The suspension was stirred over anhydrous sodium sulfate, filtered through a pad of celite, and the filter cake was washed with tetrahydrofuran. The filtrate was concentrated to give 6.74 g, (96.0%) of 2-(4-methoxyphenyl)pyrrolidine.

To a suspension of pentane washed sodium hydride (80% oil dispersion, 2.51 g) in dry dimethylformamide (50 ml) was added 2-(4-methoxyphenyl)pyrrolidine (6.74 g) in dimethylformamide (80 ml), followed by N-(2-chloroethyl)morpholine hydrochloride (7.23 g) and potassium iodide (0.05 g) at ambient temperature. The solution was heated at 110° C. for 1.5 hrs, cooled to ambient temperature, and quenched with saturated aqueous ammonium chloride solution. The mixture was distilled through a Kugelrohr apparatus. The residue was diluted with water and ethyl acetate. The layers were separated, and the aqueous phase was extracted with ethyl acetate (4 times). The combined organic extracts were washed with brine, dried over anhydrous potassium carbonate, filtered, and the filtrate was concentrated. The residue was purified by flash column chromatography (silica gel, 2% triethylamine/1% methanol/ethyl acetate). The appropriate fractions were collected and concentrated to afford 3.99 g (34.6%) of 1-[2-(4-morpholinyl)ethyl]-2-(4-methoxyphenyl)pyrrolidine. 1-[2-(4-Morpholinyl)ethyl]-2-(4-methoxyphenyl)pyrrolidine (3.75 g) was dissolved in 48% hydrobromic acid (35 ml) and warmed at 110° C. for 5 hrs. The reaction mixture was cooled, neutralized with saturated sodium bicarbonate solution and extracted into dichloromethane (6 times). The combined organic extracts were washed with brine, dried over anhydrous sodium sulfate, filtered, and the filtrate was concentrated. The residue was purified by flash column chromatography. The appropriate fractions were collected and concentrated to afford 2.36 g (66.0%) of product. The analytical sample was recrystallized from ether/petroleum ether and had mp 107°–108° C.

Analysis: Calculated for $C_{16}H_{24}N_2O_2$: 69.53%C 8.75%H 10.14%N Found: 69.32%C 8.77%H 10.06%N

EXAMPLE 12

4-{1-[2-(4-Morpholinyl)ethyl]-2-pyrrolidinyl}phenyl methylcarbamate bis-fumarate To a solution of 4-{1-[2-(4-morpholinyl)ethyl]-2-pyrrolidinyl}phenol (0.92 g) in dry tetrahydrofuran (50 ml) was added methyl isocyanate (0.22 ml) at ambient temperature, with stirring, over ten mins. Milled potassium carbonate (0.55 g) was added and the reaction mixture was stirred for 2 days and filtered through a pad of celite. The filter cake was washed with ethyl acetate and the combined filtrates concentrated. The residue was purified by flash column chromatography (silica gel, 10% methanol/ether). The appropriate fractions were collected and concentrated. The residue was dissolved in dichloromethane and washed with water (5–6 times). The combined aqueous layers were back-extracted with ether, and the combined organic extracts were washed with brine, dried over anhydrous sodium sulfate, and filtered. The filtrate was concentrated. Fumaric acid (2.02 equivalents) in absolute ethanol and diisopropyl ether was added to the residue to yield (0.55 g, 57.7%) of product, mp 119°–121° C.

Analysis: Calculated for $C_{26}H_{35}N_3O_{11}$: 55.22%C 6.24%H 7.43%N Found: 54.84%C 6.15%H 7.22%N

EXAMPLE 13

3-[1-((4-Pyridinyl)methyl)-5-oxo-2-pyrrolidinyl]phenyl methylcarbamate hemifumarate To a suspension of petroleum ether washed sodium hydride (80% oil dispersion, 0.94 g) in dry dimethylformamide (30 ml) was added 5-(3-methoxyphenyl)-2-pyrrolidinone (2.5 g) followed by 4-picolyl chloride hydrochloride (2.3 g) at ambient temperature, under nitrogen. The solution was warmed at 60° C. for 0.5 hr and allowed to cool to ambient temperature. The reaction mixture was quenched with ammonium chloride solution, water, and ethyl acetate. The layers were separated and the aqueous phase was extracted with ethyl acetate (5 times). The combined organic extracts were concentrated, the residue was diluted with a small volume of ethyl acetate, and the solution was washed with water (2 times). The organic phase was dried over anhydrous sodium sulfate, filtered, and the filtrate was concentrated to give 2.9 g (78%) of 1-(4-pyridinylmethyl)-5-(3-methoxyphenyl)-2-pyrrolidinone. 1-(4-pyridinylmethyl)-5-(3-methoxyphenyl)-2-pyrrolidinone (2.9 g) in 48% hydrobromic acid (40 ml) was heated at 100° C. for 5.5 hrs. The reaction mixture was cooled to ambient temperature, neutralized with saturated sodium bicarbonate solution, and extracted with dichloromethane (3 times). The combined organic extracts were dried over anhydrous sodium sulfate, filtered, and the filtration was concentrated. The residue was purified by flash column chromatography (silica gel, ether/0–20% methanol). The appropriate fractions were collected and concentrated to give 2.3 g (81%) of 1-(4-pyridinylmethyl)-5-(3-hydroxyphenyl)-2-pyrrolidinone.

To a solution of 1-(4-pyridinylmethyl)-5-(3-hydroxyphenyl)-2-pyrrolidinone (1.4 g) in dry tetrahydrofuran (50 ml) was added methyl isocyanate (0.34 ml) at ambient temperature, with stirring, over ten mins. Milled potassium carbonate (0.79 g) was added, and the reaction mixture was stirred for 21 hrs and filtered through a pad of celite. The filter cake was washed with ethyl acetate and the combined filtrates were concentrated. The residue was purified by flash column chromatography (silica gel, ether/0–20% methanol). The appropriate fractions were collected and concentrated to give 1.6 g (95%) of product free base. The hemifumarate salt was prepared in ethanol with fumaric acid and had mp 149°–151° C.

Analysis: Calculated for: $C_{20}H_{21}N_3O_5$: 62.65%C 5.52%H 10.96%N Found: 62.40%C 5.49%H 10.75%N

EXAMPLE 14

5-(3-Hydroxyphenyl)-1-(4-pyridinylmethyl)-2-pyrrolidinone

To a suspension of petroleum ether washed sodium hydride (80% oil dispersion, 0.94 g) in dry dimethylformamide (30 ml) was added 5-(3-methoxyphenyl)-2-pyrrolidinone (2.5 g) followed by 4-picolyl chloride hydrochloride (2.3 g) at ambient temperature, under nitrogen. The solution was warmed at 60° C. for 0.5 hr and allowed to cool to ambient temperature. The reaction mixture was quenched with ammonium chloride solution, water, and ethyl acetate. The layers were separated, and the aqueous phase was extracted with ethyl acetate (5 times). The combined organic extracts were concentrated, the residue was diluted with a small volume of ethyl acetate, and the solution was washed with water (2 times). The organic phase was dried over anhydrous sodium sulfate, filtered, and the filtrate was concentrated to give 2.9 g (78%) of 5-(3-methoxyphenyl)-1-(4-pyridinylmethyl)-2-pyrrolidinone.

A solution of 5-(3-methoxyphenyl)-1-(4-pyridinylmethyl)-2-pyrrolidinone (2.9 g) and 48% hydrobromic acid (40 ml) was heated at 100° C. for 5.5 hrs. The reaction mixture was cooled to ambient temperature, neutralized with saturated sodium bicarbonate solution and extracted with dichloromethane (3 times). The combined organic extracts were dried over anhydrous sodium sulfate, filtered, and the filtrate was concentrated. The residue was purified by flash column chromatography (silica gel, ether/0–20% methanol). The appropriate fractions were collected and concentrated to give 2.3 g (81%) of product. Recrystallization from ether/methanol gave the analytical sample, mp 148°–150° C.

Analysis: Calculated for $C_{16}H_{16}N_2O_2$: 71.62%C 6.01%H 10.44%N Found: 71.42%C 5.96%H 10.40%N

EXAMPLE 15

3-[1-Ethyl-2-pyrrolidinyl]phenyl methylcarbamate

To a solution of 5-(3-methoxyphenyl)-2-pyrrolidinone (7.0 g) in dry tetrahydrofuran (280 ml) was added lithium aluminum hydride (55 ml of 1.0M soln.) dropwise at ambient temperature, under nitrogen. The reaction mixture was warmed under reflux for 2 hrs. After cooling to ambient temperature, the reaction was quenched with 10% aqueous tetrahydrofuran (60 ml) followed by 10% sodium hydroxide solution (50 ml). The suspension was filtered through a pad of celite and the filter cake was washed with dichloromethane. The combined filtrates were concentrated. The concentrate was dried over anhydrous potassium carbonate, and filtered. The filtrate was concentrated to give 6.3 g (96%) of 2-(3-methoxyphenyl)pyrrolidine.

To a solution of 2-(3-methoxyphenyl)pyrrolidine (3.5 g) in dry acetonitrile (60 ml) was added milled potassium carbonate (4.1 g), followed by iodoethane (1.3 ml) at ambient temperature, under nitrogen, with stirring for 7 hrs. The reaction mixture was filtered through a pad of celite and the filter cake was washed with ethyl acetate. The combined filtrates were concentrated and the residue was diluted with 48% hydrobromic acid (30 ml) and warmed at 100° C. for 3.5 hrs. Upon cooling to ambient temperature, the reaction mixture was neutralized with saturated sodium bicarbonate solution and the filtrate was extracted with dichloromethane (2 times). The combined organics were dried over anhydrous sodium sulfate, filtered, and concentrated. The residue was purified by flash column chromatography (silica gel, dichloromethane/0–10% methanol). The appropriate fractions were collected and concentrated to give 0.8 g (26%) of 3-[1-ethyl-2-pyrrolidinyl]phenol.

To a solution of 3-[1-ethyl-2-pyrrolidinyl]phenol (0.8 g) in dry tetrahydrofuran (40 ml) was added methyl isocyanate (0.26 ml) at ambient temperature, under nitrogen, with stirring for ten mins. Milled potassium carbonate was added and the reaction mixture was stirred for 4 hrs, and filtered through a pad of celite. The solids were washed with ethyl acetate, and the combined filtrates were concentrated. The residue was purified by flash column chromatography (silica gel, dichloromethane/0–30% methanol), and the eluant flushed through alumina (ethyl acetate) to give 1.0 g (96%) of product. Recrystallization from ether/petroleum ether gave the analytical sample, mp 67°–69° C.

Analysis: Calculated for $C_{14}H_{20}N_2O_2$: 67.72%C 8.12%H 11.28%N Found: 67.44%C 7.98%H 11.70%N

EXAMPLE 16

3-[1-(2-Pyridinylmethyl)-2-pyrrolidinyl]phenol

To a solution of 5-(3-methoxyphenyl)-2-pyrrolidinone (7.0 g) in dry tetrahydrofuran (280 ml) was added 1M lithium aluminum hydride in tetrahydrofuran (55 ml) dropwise at ambient temperature, under nitrogen. The reaction mixture was warmed under reflux for 21 hrs, cooled to ambient temperature, and quenched with 10% aqueous tetrahydrofuran (60 ml) followed by 10% sodium hydroxide solution (50 ml). The suspension was filtered through a pad of celite, and the filter cake was washed with dichloromethane. The combined filtrates were dried over anhydrous potassium carbonate, filtered, and concentrated to give 6.3 g (96%) of 2-(3-methoxyphenyl)pyrrolidine.

To a solution of 2-(3-methoxyphenyl)pyrrolidine (3.0 g) in dry acetonitrile (70 ml) was added milled potassium carbonate (6.1 g) followed by 2-picolyl chloride hydrochloride (3.1 g) at ambient temperature, under nitrogen, with stirring for 65 hrs. The reaction mixture was filtered through a pad of celite, and the filter cake was washed with ethyl acetate. The combined filtrates were concentrated and the residue was purified by flash column chromatography (silica gel, 5% methanol/ether). The appropriate fractions were collected and concentrated to give 4.1 g (91%) of 2-(3-methoxyphenyl)-1-(2-pyridinylmethyl)pyrrolidine.

2-(3-Methoxyphenyl)-1-(2-pyridinylmethyl)pyrrolidine and 48% hydrobromic acid (40 ml) were warmed to 100° C. for 7 hrs, cooled to ambient temperature, and neutralized with saturated sodium bicarbonate solution. The mixture was extracted with dichloromethane (2 times). The combined organic extracts were dried over anhydrous sodium sulfate, filtered, and the filtrate was concentrated. The residue was purified by flash column chromatography (silica gel, 1:1 ethyl acetate/dichloromethane). The appropriate fractions were collected and concentrated to give 2.7 g (69%) of product, mp 96°–98° C.

Analysis: Calculated for $C_{16}H_{18}N_2O$: 75.56%C 7.13%H 11.0%N Found: 75.54%C 7.28%H 10.91%N

EXAMPLE 17

3-[1-(3-Pyridinylmethyl)-2-pyrrolidinyl]phenol

To a solution of 5-(3-methoxyphenyl)-2-pyrrolidinone (7.0 g) in dry tetrahydrofuran (280 ml) was added 1M lithium aluminum hydride in tetrahydrofuran (55 ml) dropwise at ambient temperature, under nitrogen. The reaction mixture was warmed under reflux for 2 hrs, cooled to ambient temperature, and quenched with 10% aqueous tetrahydrofuran (60 ml), followed by 10% sodium hydroxide solution (50 ml). The suspension was filtered through a pad of celite, and the filter cake was washed with dichloromethane. The combined filtrates were concentrated, dried over anhydrous potassium carbonate and filtered. The filtrate was concentrated to give 6.3 g (96%) of 2-(3-methoxyphenyl)pyrrolidine.

To a solution of 2-(3-methoxyphenyl)pyrrolidine (3.0 g) in dry acetonitrile (70 ml) was added milled potassium carbonate (6.1 g) followed by 3-picolyl chloride hydrochloride (3.1 g) at ambient temperature, under nitrogen, with stirring. The reaction mixture was stirred for 65 hrs, filtered through a pad of celite, and the filter cake was washed with ethyl acetate. The combined filtrates were concentrated, and the residue was purified by flash column chromatography (silica gel, 5% methanol/ether). The appropriate fractions were collected and concentrated to give 3.7 g (83%) of 2-(3-methoxyphenyl)-1-(3-pyridinylmethyl)pyrrolidine.

2-(3-Methoxyphenyl)-1-(3-pyridinylmethyl)pyrrolidine and 48% hydrobromic acid (35 ml) were warmed to 100° C. for 7 hrs. The reaction mixture was cooled to ambient temperature, neutralized with saturated sodium bicarbonate solution, and extracted with dichloromethane (2 times). The combined organic extracts were dried over anhydrous sodium sulfate, filtered, and the filtrate was concentrated. The residue was purified by flash column chromatography (silica gel, 1:1 ethyl acetate/dichloromethane). The appropriate fractions were collected and concentrated to give 2.2 g (63%) of product, mp 129°–131° C.

Analysis: Calculated for $C_{16}H_{18}N_2O$: 75.56%C 7.13%H 11.01%N Found: 75.40%C 7.02%H 11.02%N

EXAMPLE 18

4-Chloro-N-{2-[2-(3-methoxyphenyl)-1-pyrrolidinyl]ethyl}benzamide

To a solution of 2-{2-[2-(3-methoxyphenyl)-1-pyrrolidinyl]ethyl}-1H-isoindole-1,3(2H)dione (0.92 g) in ethanol (30 ml) and chloroform (5 ml) was added anhydrous hydrazine (98%, 0.42 ml) at ambient temperature, under nitrogen. The reaction mixture was warmed under reflux for 1.5 hrs, cooled to ambient temperature, and filtered. The filter cake was washed with ethanol and the combined filtrates were concentrated. The residue was diluted with dichloromethane/ether. The organic solvents were decanted and concentrated to give N-(2-aminoethyl)-2-(3-methoxyphenyl)pyrrolidine.

To a solution of N-(2-aminoethyl)-2-(3-methoxyphenyl)pyrrolidine (0.58 g) in acetonitrile (15 ml) was added milled potassium carbonate (1.10 g) followed by 4-chlorobenzoyl chloride (0.33 ml) at ambient temperature, under nitrogen. The reaction mixture was stirred for 1.5 hrs, diluted with dichloromethane, and filtered. The filter cake was washed with dichloromethane, and the combined filtrates were concentrated. The residue was purified by flash column chromatography (silica gel, 0–20% methanol/dichloromethane). The appropriate fractions were collected and concentrated to afford 0.80 g (85%) of product. Trituration with ether/petroleum ether gave the analytical sample, mp 96°–98° C.

Analysis: Calculated for $C_{20}H_{23}ClN_2O_2$: 66.94%C 6.46%H 7.81%N Found: 66.93%C 6.30%H 7.70%N

EXAMPLE 19

3-{1-[2-[(4-Chlorobenzoyl)amino]ethyl]-2-pyrrolidinyl}phenyl methylcarbamate To a solution of 4-chloro-N-{2-[2-(3-methoxyphenyl)-1-pyrrolidinyl]ethyl}benzamide (0.58 g) in chloroform (30 ml) was added boron tribromide (99.0%, 0.61 ml) at −10° C., under nitrogen. The cooling bath was removed after 15 mins, and the reaction mixture was allowed to warm to ambient temperature. Crushed ice was added followed by 5:1-chloroform/2-propanol. The layers were separated, and the aqueous phase was extracted with 5:1 chloroform/2-propanol (2 times). The combined organic extracts were washed with saturated sodium bicarbonate, dried over anhydrous sodium sulfate, filtered, and the filtrate was concentrated. The residue was purified by flash column chromatography (silica gel, 30% ethyl acetate/dichloromethane). The appropriate fractions were collected and concentrated to afford 0.29 g (52%) of 4-chloro-N-{2-[2-(3-hydroxyphenyl)-1-pyrrolidinyl]ethyl}benzamide.

The 4-chloro-N-{2-[2-(3-hydroxyphenyl)-1-pyrrolidinyl]ethyl}benzamide (0.29 g) was dissolved in tetrahydrofuran (20 ml), and methyl isocyanate (50.0 µl) and milled potassium carbonate (0.17 g) at ambient temperature were added, under nitrogen. The reaction mixture was stirred for 2 hrs and filtered through a pad of celite. The filter cake was washed with ethyl acetate, and the combined filtrates were concentrated. Crystallization of the residue with ether/petroleum ether gave 0.32 g (94%) of product. Recrystallization from ether gave the analytical sample, mp 103°–106° C.

Analysis: Calculated for $C_{21}H_{24}ClN_3O_3$: 62.76%C 6.02%H 10.46%N Found: 62.77%C 5.75%H 10.40%N

EXAMPLE 20

3-[1-Benzoyl-2-pyrrolidinyl]phenol

To a solution of 5-(3-methoxyphenyl)-2-pyrrolidinone (7.0 g) in dry tetrahydrofuran (280 ml) was added 1M lithium aluminum hydride in tetrahydrofuran (55 ml) dropwise, at ambient temperature, under nitrogen. Upon completion of the addition, the reaction mixture was heated under reflux for 2 hrs, cooled to ambient temperature, and quenched with 10% aqueous tetrahydrofuran (60 ml) followed by 10% sodium hydroxide solution (50 ml). The suspension was filtered through a pad of celite, and the filter cake was washed with dichloromethane. The combined filtrates were concentrated. The concentrate was dried over anhydrous potassium carbonate, filtered, and the filtrate was concentrated to give 6.3 g (96%) of 2-(3-methoxyphenyl)pyrrolidine.

To a solution of 2-(3-methoxyphenyl)pyrrolidine (1.0 g) in dry acetonitrile (50 ml) was added milled potassium carbonate (2.0 g) followed by benzoyl chloride (0.73 ml) at ambient temperature, under nitrogen. The reaction mixture was stirred for 2 hrs, filtered through a pad of celite, and the filter cake was washed with ethyl acetate. The combined filtrates were concentrated, and the residue was purified by flash column chromatography (silica gel, 0–25% ethyl acetate/dichloromethane). The appropriate fractions were collected and concentrated to give 1.2 g (75%) of 1-benzoyl-2-(3-methoxyphenyl)pyrrolidine.

To a solution of 1-benzoyl-2-(3-methoxyphenyl)pyrrolidine (1.0 g) in chloroform (40 ml) was added boron tribromide (99%, 1.0 ml) at −10° C., under nitrogen. The cooling bath was removed after 15 mins, and the reaction mixture was allowed to warm to ambient temperature. Crushed ice was added to the reaction mixture followed by 5:1-chloroform/2-propanol. The layers were separated, and the aqueous phase was extracted with 5:1-chloroform/2-propanol (2 times). The combined organic extracts were washed with saturated sodium bicarbonate solution, dried over anhydrous sodium sulfate, filtered, and the filtrate was concentrated. The residue was crystallized from dichloromethane/petroleum ether to give 0.89 g (94 %) of product. Recrystallization from 2-propanol/methanol gave the analytical sample, mp 167°–169° C.

Analysis: Calculated for $C_{17}H_{17}NO_2$: 76.38%C 6.41%H 5.24%N Found: 76.35%C 6.38%H 5.33%N

EXAMPLE 21

3-(1-Benzoyl-2-pyrrolidinyl)phenyl methylcarbamate

To a solution of 3-[1-benzoyl-2-pyrrolidinyl]phenol (0.69 g) in dry tetrahydrofuran (35 ml) was added methyl isocyanate (0.16 ml) followed by milled potassium carbonate (0.46 g) at ambient temperature, under nitrogen. The reaction mixture was stirred for 22 hrs, at which time it was filtered through a pad of celite, and the solids washed with ethyl acetate. The combined filtrates were concentrated. Recrystallization of the residue from ethyl acetate afforded 0.50 g (60%) of product, mp 117°–121° C.

Analysis: Calculated for $C_{19}H_{20}N_2O_3$: 70.35%C 6.21%H 8.64%N Found: 70.22%C 6.21%H 8.59%N

EXAMPLE 22

2-{2-[2-(3-Methoxyphenyl)-1-pyrrolidinyl]ethyl}-1H-isoindole-1,3(2H)dione

To a solution of 5-(3-methoxyphenyl)-2-pyrrolidinone (7.0 g) in dry tetrahydrofuran (280 ml) was added 1M lithium aluminum hydride in tetrahydrofuran (55 ml), dropwise at ambient temperature, under nitrogen. Upon completion of the addition, the reaction mixture was warmed under reflux for 2 hrs, cooled to ambient temperature, and quenched with 10% aqueous tetrahydrofuran (60 ml) followed by 10% sodium hydroxide solution (50 ml). The suspension was filtered through a pad of celite, and the filter cake was washed with dichloromethane. The combined filtrates were dried over anhydrous potassium carbonate, filtered, and the filtrate was concentrated to give 6.3 g (96%) of 2-(3-methoxyphenyl)pyrrolidine.

To a solution of 2-(3-methoxyphenyl)pyrrolidine (1.9 g) in dry acetonitrile (50 ml) was added N-(2-bromoethyl)phthalimide (3.6 g) followed by milled potassium carbonate (3.8 g) and potassium iodide (catalytic amount) at ambient temperature, under nitrogen. The reaction mixture was warmed under reflux for 18.5 hrs, cooled to ambient temperature and filtered through a pad of celite. The filter cake was washed with ethyl acetate, and the combined filtrates were concentrated. The residue was diluted with ether and methanol, the mixture was filtered, and the filtrate was concentrated. The residue was purified by flash column chromatography (silica gel, dichloromethane). The appropriate fractions were collected and concentrated to afford a total 2.1 g (54%) of product. Recrystallization from ether gave the analytical sample, mp 110°–111° C.

Analysis: Calculated for $C_{21}H_{22}N_2O_3$: 71.98%C 6.33%H 7.99%N Found: 71.58%C 6.29%H 7.97%N

EXAMPLE 23

2-{2-[2-(3-Hydroxyphenyl)-1-pyrrolidinyl]ethyl}-1H-isoindole-1,3(2H)dione

To a solution of 2-{2-[2-(3-methoxyphenyl)-1-pyrrolidinyl]ethyl}-1H-isoindole-1,3(2H)dione (1.0 g), in dry chloroform (40 ml) was added boron tribromide (99%, 1.3 ml) at −10° C., under nitrogen. The reaction mixture was stirred for 10 mins in a cooling bath and 20 mins at ambient temperature. Crushed ice was added followed by 5:1-chloroform/2-propanol (10 ml). The layers were separated, and the aqueous phase was extracted with 5:1-chloroform/2-propanol (2 times). The combined organic extracts were washed with saturated sodium bicarbonate solution, dried over anhydrous sodium sulfate, filtered, and the filtrate was concentrated to give 0.89 g (93%) of product, mp 172°–175° C.

Analysis: Calculated for $C_{20}H_{20}N_2O_3$: 71.41%C 5.99%H 8.33%N Found: 70.17%C 5.56%H 7.97%N

EXAMPLE 24

3-{1-[2-(1,3-Dihydro-1,3-dioxo-2H-isoindol-2-yl)ethyl]-2-pyrrolidinyl}phenyl methylcarbamate To a solution of 2-{2-[2-(3-hydroxyphenyl)-1-pyrrolidinyl]ethyl}-1H-isoindole-1,3(2H)dione (0.71 g) in dry tetrahydrofuran (35 ml) was added methyl isocyanate (0.13 ml) followed by milled potassium carbonate (0.38 g) at ambient temperature, under nitrogen. The reaction mixture was stirred for 45 mins, filtered through a pad of celite, and the filter cake was washed with ethyl acetate. The combined filtrates were concentrated, and the residue was triturated with petroleum ether. The residue was purified by flash column chromatography (silica gel, 1:1 ethyl acetate/heptane). The appropriate fractions were collected and concentrated to afford 0.78 g (94%) of product. Recrystallization from dichloromethane/petroleum ether gave the analytical sample, mp 96°–98° C.

Analysis: Calculated for $C_{22}H_{23}N_3O_4$: 67.16%C 5.89%H 10.68%N Found: 66.99%C 5.66%H 10.45%N

EXAMPLE 25

3-[1-(2-Phenylethyl)-2-pyrrolidinyl]phenyl methylcarbamate

To a solution of 5-(3-methoxyphenyl)-2-pyrrolidinone (7.0 g) in dry tetrahydrofuran (280 ml) was added 1M lithium aluminum hydride in tetrahydrofuran (55 ml), dropwise at ambient temperature, under nitrogen. Upon completion of the addition, the reaction mixture was warmed under reflux for 2 hrs, cooled to ambient temperature, and quenched with 10% aqueous tetrahydrofuran (60 ml) followed by 10% sodium hydroxide solution (50 ml). The resulting suspension was filtered through a pad of celite, and the filter cake was washed with dichloromethane. The combined filtrates were dried over anhydrous potassium carbonate, filtered, and the filtrate was concentrated to give 6.3 g (96%) of 2-(3-methoxyphenyl)pyrrolidine.

To a solution of 2-(3-methoxyphenyl)pyrrolidine (1.04 g) in dry acetonitrile (30 ml) was added 2-bromoethylbenzene (0.96 ml) followed by milled potassium carbonate (1.78 g) at ambient temperature, under nitrogen. The reaction mixture was stirred for 48 hrs, warmed under reflux for 2 hrs, and cooled to ambient temperature. The reaction mixture was filtered through a pad of celite, and the filter cake was washed with ethyl acetate. The combined filtrates were concentrated and the residue was purified by flash column chromatography (silica gel, dichloromethane/0–100% ether). The appropriate fractions were collected and concentrated to afford 1.2 g (72%) of 2-(3-methoxyphenyl)-1-(2-phenylethyl)pyrrolidine.

2-(3-Methoxyphenyl)-1-(2-phenylethyl)pyrrolidine and 48% hydrobromic acid (15 ml) were warmed to 105° C. for 3.5 hrs and cooled to ambient temperature. The reaction mixture was neutralized with saturated sodium bicarbonate solution, and the mixture was extracted with dichloromethane (2 times). The combined organic extracts were dried over anhydrous sodium sulfate, filtered, and the filtrate was concentrated. The residue was purified by flash column chromatography (silica gel, ether). The appropriate fractions were collected and concentrated to afford 1.1 g (96%) of 3-[1-(2-phenylethyl)-2-pyrrolidinyl]phenol.

To a solution of 3-[1-(2-phenylethyl)-2-pyrrolidinyl]phenol (0.83 g) in dry tetrahydrofuran (40 ml) was added methyl isocyanate (0.20 ml) followed by milled potassium carbonate (0.51 g) at ambient temperature, under nitrogen. The reaction mixture was stirred for 4 hrs, filtered through a pad of celite, and the solids were washed with ethyl acetate. The combined filtrates were concentrated, and the residue was purified by flash column chromatography (silica gel 30–75% ether/heptane). The appropriate fractions were collected and concentrated to afford 0.84 g (84%) of product. The analytical sample was prepared by flushing the compound through alumina with ether.

Analysis: Calculated for $C_{20}H_{24}N_2O_2$: 74.05%C 7.46%H 8.64%N Found: 73.73%C 7.31%H 8.87%N

EXAMPLE 26

3-[1-Phenylmethyl-2-pyrrolidinyl]phenyl octylcarbamate

To a solution of 3-(1-phenylmethyl-2-pyrrolidinyl)phenol (0.06 g) in dry tetrahydrofuran (30 ml) was added octyl isocyanate (0.44 ml) at ambient temperature, under nitrogen. The reaction mixture was stirred for 17 hrs and filtered through a pad of celite. The filter cake was washed with ethyl acetate and the combined filtrates were concentrated. The residue was purified by flash column chromatography (silica gel, dichloromethane). The appropriate fractions were collected and concentrated to give 0.50 g (52%) of product. The analytical sample was prepared by flushing the product through alumina with ether.

Analysis: Calculated for $C_{26}H_{36}N_2O_2$: 76.43%C 8.88%H 6.86%N Found: 76.77%C 8.76%H 6.69%N

EXAMPLE 27

3-(1-Phenylmethyl-2-pyrrolidinyl)phenyl 2-(4-morpholinyl)ethylcarbamate

To a solution of 3-[1-phenylmethyl-2-pyrrolidinyl]phenol (0.64 g) in dry tetrahydrofuran (20 ml) was added 1,1'-carbonyldiimidazole (0.61 g) at ambient temperature, under nitrogen. The reaction mixture was stirred for 48 hrs, glacial acetic acid (0.50 ml) was added followed by a solution of 4-(2-aminoethyl)morpholine (0.43 ml) in tetrahydrofuran (1.0 ml) and glacial acetic acid (0.20 ml). After 3 hrs, the reaction mixture was poured into saturated sodium bicarbonate solution and ether. The layers were separated, and the aqueous phase was extracted with ether (2 times). The combined organic extracts were washed with saturated sodium bicarbonate and brine, dried over anhydrous sodium sulfate, filtered, and the filtrate was concentrated. The residue was purified by radial chromatography, using ether as the eluent. The appropriate fractions were collected and concentrated to give 0.56 g (54%) of product. Recrystallization from ether/petroleum ether gave the analytical sample, mp 74°–77° C.

Analysis: Calculated for $C_{24}H_{31}N_3O_3$: 70.39%C 7.63%H 10.26%N Found: 70.25%C 7.37%H 10.51%N

EXAMPLE 28

3-[1-(3-Pyridinylmethyl)-2-pyrrolidinyl]phenyl methylcarbamate

To a solution of 3-[1-(3-pyridinylmethyl)-2-pyrrolidinyl]phenol (0.92 g) in dry tetrahydrofuran (50 ml) was added methyl isocyanate (0.22 ml) followed by milled potassium carbonate (0.65 g) at ambient temperature, under nitrogen. The reaction mixture was stirred for 13 hrs, filtered through a pad of celite, and the filter cake was washed with ethyl acetate. The combined filtrates were concentrated. The residue was purified by flash column chromatography (silica gel, ethyl acetate). The appropriate fractions were collected and concentrated to give 0.94 g (85%) of product.

Analysis: Calculated for $C_{18}H_{21}N_3O_2$: 69.43%C 6.80%H 13.49%N Found: 68.96%C 6.97%H 13.55%N

EXAMPLE 29

3-(1-Phenylmethyl-2-pyrrolidinyl)phenol

To a solution of 5-(3-methoxyphenyl)-2-pyrrolidinone (7.0 g) in dry tetrahydrofuran (280 ml) was added 1M lithium aluminum hydride in tetrahydrofuran (55 ml), dropwise at ambient temperature, under nitrogen. Upon completion of the addition, the reaction mixture was warmed under reflux for 2 hrs, cooled to ambient temperature, and quenched with 10% aqueous tetrahydrofuran (60 ml) followed by 10% sodium hydroxide solution (50 ml). The suspension was filtered through a pad of celite, and the filter cake was washed with dichloromethane. The combined filtrates were concentrated and the concentrate was dried over anhydrous potassium carbonate, filtered, and the filtrate was concentrated to give 6.3 g (96%) of 2-(3-methoxyphenyl)pyrrolidine.

To a solution of 2-(3-methoxyphenyl)pyrrolidine (3.0 g) in dry acetonitrile (70 ml) was added milled potassium carbonate (3.7 g) followed by benzyl chloride (2.2 g) at ambient temperature, under nitrogen. The reaction mixture was stirred for 5 hrs, warmed under reflux for 2 hrs, and cooled to ambient temperature. The reaction mixture was filtered through a pad of celite, and the solids washed with ethyl acetate. The combined filtrates were concentrated to give 4.3 g (96%) of 1-phenylmethyl-2-(3-methoxyphenyl)pyrrolidine.

1-Phenylmethyl-2-(3-methoxyphenyl)pyrrolidine in 48% hydrobromic acid (65 ml), was warmed to 110° C. for 2.5 hrs, and cooled to ambient temperature. The reaction mixture was neutralized with saturated sodium bicarbonate solution and extracted into dichloromethane (2 times). The combined organic extracts were dried over anhydrous sodium sulfate, filtered, and the filtrate was concentrated. The residue was purified by flash column chromatography (silica gel, 1:1 ethyl acetate/dichloromethane). The appropriate fractions were collected and concentrated. The residue was flushed through alumina with ether to give 2.5 g (61%) of product, mp 113°–115° C.

Analysis: Calculated for $C_{17}H_{19}NO$: 80.60%C 7.56%H 5.53%N Found: 80.59%C 7.58%H 5.37%N

EXAMPLE 30

3-[1-Phenylmethyl-2pyrrolidinyl]phenyl methylcarbamate

To a solution of 3-[1-phenylmethyl-2-pyrrolidinyl]phenol (1.0 g) in dry tetrahydrofuran (50 ml) was added methyl isocyanate (0.24 ml) followed by milled potassium carbonate (0.7 g) at ambient temperature, under nitrogen. The reaction mixture was stirred for 1 hr, filtered through a pad of celite, and the filter cake was washed with ethyl acetate. The combined filtrates were concentrated. The residue was purified by flash column chromatography (silica gel, dichloromethane/0–10% ethyl acetate). The appropriate fractions were collected and concentrated to give 0.8 g (70%) of product.

Analysis: Calculated for $C_{19}H_{22}N_2O_2$: 73.52%C 7.14%H 9.02%N Found: 73.75%C 7.29%H 8.63%N

EXAMPLE 31

4-{1-[2-(4-Morpholinyl)ethyl]-5-oxo-2-pyrrolidinyl}phenyl 3,4-dihydro-2(1H)-isoquinolinylcarbamate To a solution of 5-(4-hydroxyphenyl)-1-[2-(4-morpholinyl)ethyl]pyrrolidin-2-one (1.24 g), pyridine (0.73 ml), and dichloromethane (50 ml), cooled to 0° C., under nitrogen, was added triphosgene (0.43 g) in dichloromethane (10 ml). The mixture was stirred at 0° C. for 1 hr. 1,2,3,4-Tetrahydroisoquinoline (0.67 ml) was added, and the reaction mixture was allowed to warm to ambient temperature overnight. Aqueous sodium bicarbonate solution was added and the layers separated. The aqueous layer was back-extracted with dichloromethane (2 times) and ether (1 time), and the combined organic extract was washed with brine, dried over anhydrous sodium sulfate, filtered, and the filtrate was concentrated to give product.

The reaction was repeated as above, using 5-(4-hydroxyphenyl)-1-[2-(4-morpholinyl)ethyl]pyrrolidin-2-one (1.50 g) in dichloromethane (50 ml), pyridine (0.88 ml), triphosgene (0.52 g) in 10 ml dichloromethane, and 1,2,3,4-tetrahydroisoquinoline (0.78 ml). The reaction mixture was worked up as above. The two reaction mixtures were combined and purified by preparative high performance liquid chromatography (silica gel, 1% triethylamine/1-2% methanol/ethyl acetate). The appropriate fractions were collected and concentrated to afford 1.58 g (37.0%) of product. The analytical sample was prepared by recrystallization from ethyl acetate and had mp 143.5°-145.5° C.

Analysis: Calculated for $C_{26}H_{31}N_3O_4$: 69.45%C 6.96%H 9.35%N Found: 69.71%C 7.10%H 9.34%N

PHARMACEUTICAL FORMULATIONS

| TABLET | |
|---|---|
| Ingredients | In each tablet |
| 3-[1-(4-Pyridinylmethyl)-2-pyrrolidinyl]phenyl methylcarbamate | 300.0 mg |
| Polyvinylpyrrolidone | 22.5 mg |
| Lactose | 61.75 mg |
| Alcohol 3A - 200 proof | 4.5 mg |
| Stearic Acid | 9.0 mg |
| Talc | 13.5 mg |
| Corn starch | 43.25 mg |

Blend 3-[1-(4-Pyridinylmethyl)-2-pyrrolidinyl]phenyl methylcarbamate, polyvinylpyrrolidone, and lactose together; pass through a 40-mesh screen. Add the alcohol slowly and knead well. Screen the wet mass through a 4-mesh screen, dry granulation at 50° C. overnight. Screen the dried granulation through a 20-mesh screen. Bolt the stearic acid, talc, and corn starch through 60-mesh screen prior to mixing by tumbling with the granulation. Compress using 7/16-in. standard concave punch. 10 tablets should weigh 4.5 g.

| SUPPOSITORY: | |
|---|---|
| Ingredients | In each suppository |
| 3-[1-(4-Pyridinylmethyl)-2-pyrrolidinyl]phenyl methylcarbamate | 300.0 mg |
| Glycerin | 3000.0 mg |
| Purified water | 200.0 mg |

The glycerin is heated in a suitable container to about 120° C. The drug is dissolved, with gentle stirring, in the heated glycerin after which the purified water is added, mixed, and the hot mixture immediately poured into a suitable mold.

| EMULSION: | |
|---|---|
| Ingredients | Amount |
| Gelatin Type A* | 4 g |
| 3-[1-(4-Pyridinylmethyl)-2-pyrrolidinyl]phenyl methylcarbamate | 360 mg |
| Flavor as desired | |
| Alcohol | 30 ml |
| Oil | 250 ml |
| Purified water, to make | 500 ml |

*prepared from acid-treated precursors; used at a pH of ca.3.2.

Add the gelatin and the drug to about 300 ml of purified water, allow to stand for a few minutes, heat until the gelatin is dissolved, then raise the temperature to about 90° C., and maintain this temperature for about 20 mins. Cool to 50° C., and add the flavor, the alcohol, and sufficient purified water to make 500 ml. Add the oil, agitate the mixture thoroughly, and pass it through a homogenizer or a colloid mill until the oil is completely and uniformly dispersed.

REACTION SCHEME A

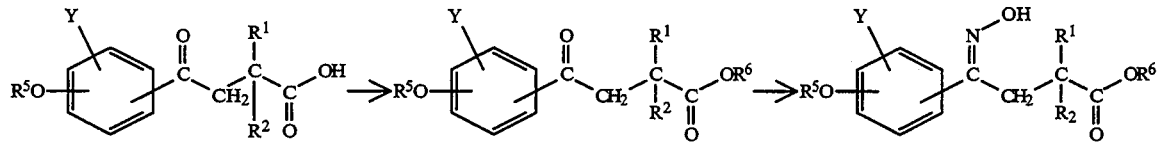

-continued
REACTION SCHEME A
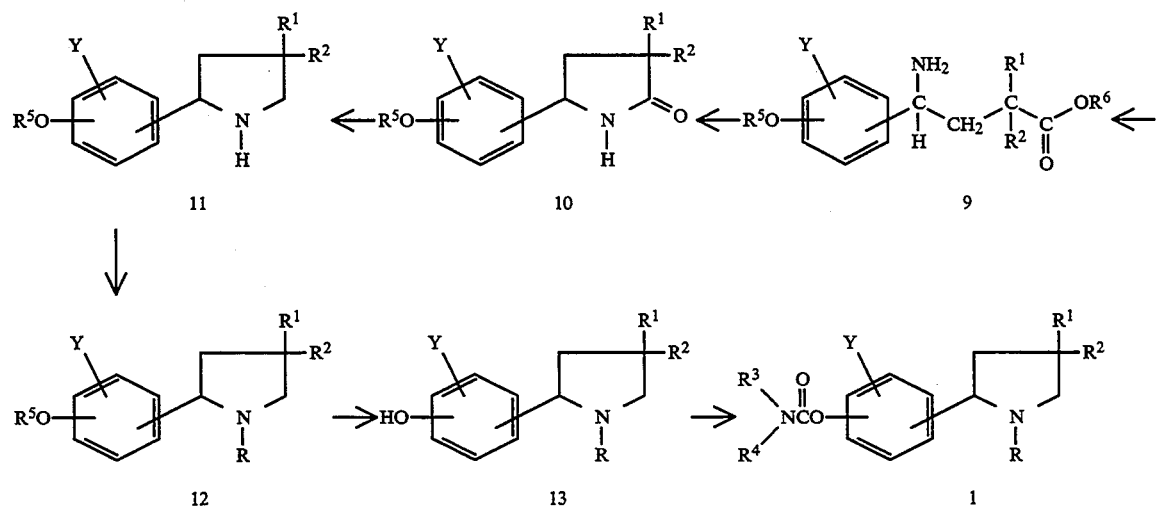
REACTION SCHEME B
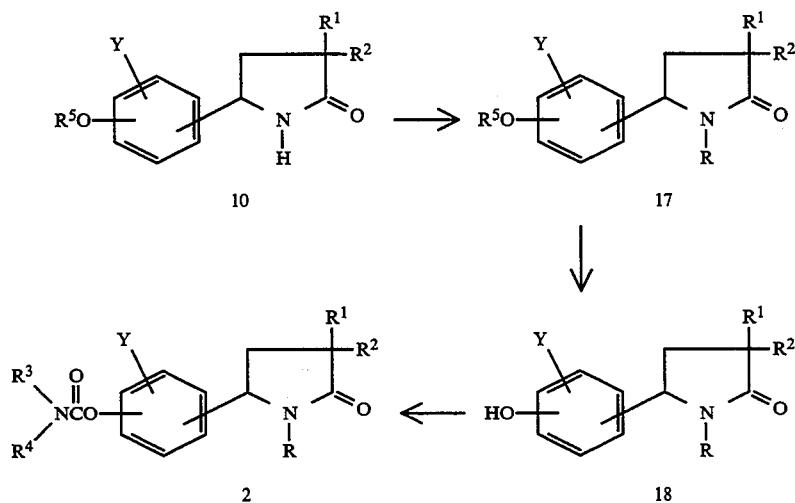
We claim:
1. A compound of the formula
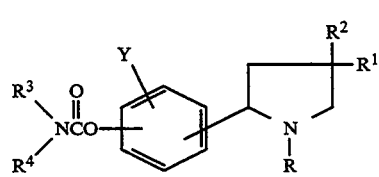
wherein:
  a. R is hydrogen, loweralkyl, a group of the formula
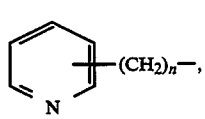
a group of the formula
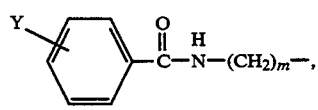
a group of the formula
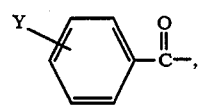
a group of the formula
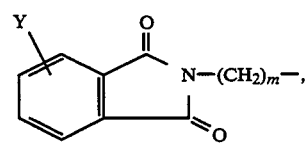
a group of the formula a group of the formula

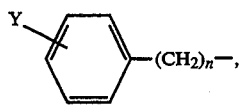

or a group of the formula

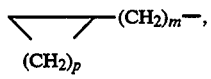

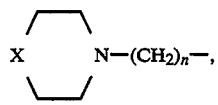

wherein X is —CH$_2$—, —O—, or —S—, Y is hydrogen, loweralkyl, loweralkoxy, hydroxy, halogen, or trifluoromethyl, and m is 1 to 5, n is 1 to 5, and p is 1,2,3,4, or 5;

b. R$^1$ and R$^2$ are independently hydrogen or loweralkyl;

c. R$^3$ and R$^4$ are independently hydrogen, loweralkyl, phenyl or phenyl substituted by one or more loweralkyl, loweralkoxy, hydroxy, halogen, or trifluoromethyl groups, or taken together with the nitrogen atom to which they are bound form a pyrrolidinyl, piperidinyl, morpholinyl, or thiomorpholinyl group, or a group of the formula

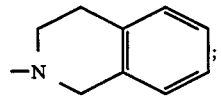

the optical isomers, or pharmaceutically acceptable salts thereof.

2. A compound according to claim 1 wherein R is loweralkyl, a group of the formula

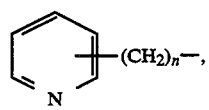

a group of the formula

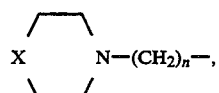

or a group of the formula

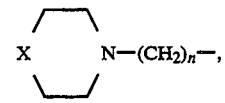

R$^3$ and R$^4$ are independently hydrogen or loweralkyl, or R$^3$ and R$^4$ taken together with the nitrogen atom to which they are bound form a group of the formula

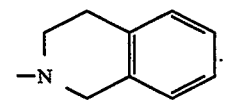

3. A compound according to claim 2 wherein X is O.

4. The compound according to claim 2 which is 3-[1-(4-pyridinylmethyl)-2-pyrrolidinyl]phenyl methylcarbamate.

5. The compound according to claim 2 which is 3-[1-(4-pyridinylmethyl)-2-pyrrolidinyl]phenyl 3,4-dihydro-2(1H)isoquinolinylcarbamate.

6. The compound according to claim 3 which is 3-{1-[2-(4-morpholinyl)ethyl]-2-pyrrolidinyl}phenyl methylcarbamate.

7. The compound according to claim 3 which is 4-{1-[2-(4-morpholinyl)ethyl]-2-pyrrolidinyl}phenyl methylcarbamate.

8. The compound according to claim 2 which is 3-(1-ethyl-2-pyrrolidinyl)phenyl methylcarbamate.

9. The compound according to claim 1 which is 3-{1-[2-(4-chlorobenzoyl)amino]ethyl-2-pyrrolidinyl}phenyl methylcarbamate.

10. The compound according to claim 1 which is 3-(1-benzoyl-2-pyrrolidinyl)phenyl methylcarbamate.

11. The compound according to claim 1 which is 3-{1-[2-(1,3-dihydro- 1,3-dioxo-2H-isoindol-2-yl)ethyl]-2-pyrrolidinyl}phenyl methylcarbamate.

12. The compound according to claim 1 which is 3-[1-(2-phenylethyl)-2-pyrrolidinyl]phenyl methylcarbamate.

13. The compound according to claim 1 which is 3-[1-(phenylmethyl)-2-pyrrolidinyl]phenyl octylcarbamate.

14. The compound according to claim 1 which is 3-(1-phenylmethyl-2-pyrrolidinyl)phenyl 2-(4-morpholinyl)ethylcarbamate.

15. The compound according to claim 1 which is 3-[1-(3-pyridinylmethyl)-2-pyrrolidinyl]phenyl methylcarbamate.

16. The compound according to claim 1 which is 3-[1-(2-phenylethyl)-2-pyrrolidinyl]phenyl methylcarbamate.

17. A method of relieving memory dysfunction in mammals comprising administering to a mammal requiring memory dysfunction relief, a memory dysfunction relieving effective amount of a compound of claim 1.

18. A memory dysfunction relieving composition comprising an adjuvant and as the active ingredient, a memory dysfunction relieving effective amount of a compound of claim 1.

* * * * *

UNITED STATES PATENT AND TRADEMARK OFFICE
CERTIFICATE OF CORRECTION

PATENT NO. : 5,338,739
DATED : 08/16/94
INVENTOR(S) : David G. Wettlaufer and Peter A. Nemoto It is certified that error appears in the above—identified patent and that said Letters Patent is hereby corrected as shown below:

Claim 2, column 35, line 49, which is blank, should read

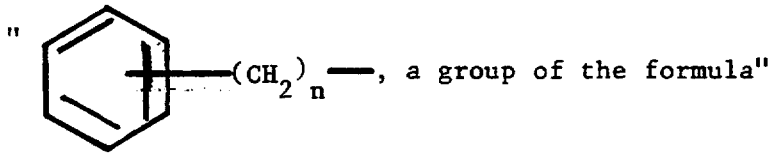

Column 35, line 55, insert "or" before --a--
Column 35, line 65, delete "or a group of the formula"
Column 36, lines 1-5, delete the formula.

Signed and Sealed this

Twenty-fifth Day of June, 1996

Attest:

BRUCE LEHMAN

Attesting Officer    Commissioner of Patents and Trademarks